(12) United States Patent
Simpson et al.

(10) Patent No.: US 7,417,749 B1
(45) Date of Patent: Aug. 26, 2008

(54) METHOD AND APPARATUS FOR PROTECTING AN OPTICAL TRANSMISSION MEASUREMENT WHEN SENSING TRANSPARENT MATERIALS

(75) Inventors: Jeffrey A. Simpson, Wayne, NE (US); Mark A. Imbrock, Sylvania, OH (US)

(73) Assignee: Electric Design to Market, Inc., Wayne, NE (US)

( * ) Notice: Subject to any disclaimer, the term of this patent is extended or adjusted under 35 U.S.C. 154(b) by 293 days.

(21) Appl. No.: 11/217,508

(22) Filed: Sep. 1, 2005

Related U.S. Application Data

(60) Provisional application No. 60/606,454, filed on Sep. 1, 2004.

(51) Int. Cl.
*G01B 11/06* (2006.01)

(52) U.S. Cl. .................. 356/632; 356/445; 356/630; 250/559.29; 250/559.39

(58) Field of Classification Search ............... 356/381, 356/382, 445, 630–632; 250/559.28, 559.39, 250/338, 219
See application file for complete search history.

(56) References Cited

U.S. PATENT DOCUMENTS

| | | | |
|---|---|---|---|
| 1,503,543 A | 8/1924 | Lytle | |
| 1,756,785 A | 4/1930 | Gallasch | |
| 3,016,464 A | 1/1962 | Bailey | 250/219 |
| 3,137,756 A | 6/1964 | Gunther et al. | 88/14 |
| 3,693,025 A | 9/1972 | Brunton | 250/83.3 H |
| 3,807,870 A * | 4/1974 | Kalman | 356/630 |
| 3,994,586 A | 11/1976 | Sharkins et al. | 356/73 |
| 4,207,467 A | 6/1980 | Doyle | 250/338 |
| 4,284,356 A | 8/1981 | Heilman | 250/559.39 |
| 4,848,913 A | 7/1989 | Greiner | 356/382 |
| 4,899,055 A | 2/1990 | Adams | 250/372 |
| 4,902,902 A | 2/1990 | Tole | 250/559.28 |
| 4,984,894 A | 1/1991 | Kondo | 356/382 |
| 5,054,927 A | 10/1991 | Garves | 356/382 |
| 5,132,631 A | 7/1992 | Klopfenstein et al. | |
| 5,237,392 A | 8/1993 | Hickel et al. | 356/381 |
| 5,239,488 A | 8/1993 | Markham et al. | 364/557 |
| 5,254,149 A | 10/1993 | Hashemi et al. | 65/29 |
| 5,442,573 A | 8/1995 | Bredberg et al. | 364/563 |

(Continued)

FOREIGN PATENT DOCUMENTS

DE     22584     1/1962

(Continued)

*Primary Examiner*—Gregory J. Toatley, Jr.
*Assistant Examiner*—Iyabo S Alli
(74) *Attorney, Agent, or Firm*—MacMillan Sobanski & Todd, LLC

(57) ABSTRACT

A method and apparatus for protecting an optical transmission measurement when sensing transparent materials. Sensing apparatus located in a housing directs a light beam at an upward angle to a sheet of transparent material and detects downward surface reflections of the beam from the transparent material. The light beam and the reflections pass through a transparent protective layer on the housing. A flow of clean air is passed between the protective layer and the transparent material to remove particles and liquid from the protective layer and from the space between the protective layer and the transparent material. Preferably, the protective layer is either made from a hydrophobic material or has a hydrophobic surface coating to facilitate blowing liquid and particles from the surface.

6 Claims, 1 Drawing Sheet

U.S. PATENT DOCUMENTS

| | | | |
|---|---|---|---|
| 5,490,728 A | 2/1996 | Schietinger et al. | 374/7 |
| 5,525,138 A | 6/1996 | Hashemi et al. | 65/29.18 |
| 5,564,830 A | 10/1996 | Bobel et al. | 374/126 |
| 5,568,264 A | 10/1996 | Nakatsuka et al. | 356/394 |
| 5,581,355 A | 12/1996 | Myers et al. | 356/382 |
| 5,597,237 A | 1/1997 | Stein | 374/9 |
| 5,637,873 A | 6/1997 | Davis et al. | 250/339.11 |
| 5,657,124 A | 8/1997 | Zhang et al. | 356/355 |
| 5,726,749 A | 3/1998 | Schave | 356/239 |
| 5,726,756 A | 3/1998 | Aki et al. | 356/381 |
| 5,727,017 A | 3/1998 | Maurer et al. | 374/9 |
| 5,748,091 A | 5/1998 | Kim | 340/583 |
| 5,838,446 A | 11/1998 | Meth et al. | 356/372 |
| 5,966,214 A | 10/1999 | Imbrock et al. | 356/632 |
| 6,683,695 B1 | 1/2004 | Simpson et al. | 356/632 |
| 6,916,507 B2 * | 7/2005 | Matsumura et al. | 427/440 |
| 6,921,431 B2 * | 7/2005 | Evans et al. | 252/70 |

FOREIGN PATENT DOCUMENTS

| | | |
|---|---|---|
| EP | 0 480 027 | 4/1992 |
| GB | 2321309 | 7/1998 |
| JP | 53-16652 | 2/1978 |
| JP | 56-44804 | 4/1981 |
| JP | 60-147606 | 8/1985 |
| RU | 1585670 | 8/1990 |

* cited by examiner

METHOD AND APPARATUS FOR PROTECTING AN OPTICAL TRANSMISSION MEASUREMENT WHEN SENSING TRANSPARENT MATERIALS

CROSS-REFERENCE TO RELATED APPLICATIONS

Applicants claim priority to U.S. Provisional Patent Application Ser. No. 60/606,454 filed Sep. 1, 2004.

STATEMENT REGARDING FEDERALLY SPONSORED RESEARCH OR DEVELOPMENT

Not Applicable.

TECHNICAL FIELD

In a system that uses reflected light beam(s) for measuring physical properties of a transparent medium to determine a physical property such as the presence and location of a surface coating or the thickness of the medium under test, a method and apparatus to maintain signal sensing quality and to remove contaminants from the sensing path.

BACKGROUND OF THE INVENTION

In the glass industry, for example, there are applications where a transparent material such as glass must be measured for thickness for the manufacturing of windows or for the location of coated surfaces such as the surface location of a LOW-E energy efficient coating that has been applied to one side of the glass. One method for measuring glass properties is to direct a light beam at an angle to a surface of the glass and sensing the location and intensity of reflections of the light beam from the surfaces of the glass. The reflections will be influenced by factors including the spacing between the glass surfaces, the presence, location and nature of any coatings on the glass surfaces and the wave length of the light beam.

The light beam and the reflected light signals will often be transmitted through a path which includes contaminated air, water, and the coated transparent surfaces being tested. The signal quality received from an optical system working in multiple environments that may be affected by air borne or liquid contaminants must be preserved to reduce the amount of labor necessary to maintain that system. Different environments in which glass properties are measured may include, for example, glass cutting tables with the possibility of air borne glass particles, large factory environments with HVAC or fan systems moving contaminated air through the environment, liquids that are used to wash the glass to remove Lucor (separating powders) and oil residues from the glass. Routine factory maintenance is used to clean the manufacturing area, but this can leave the possibility of lower quality product being manufactured as the sensing environment is diminished until a failure condition occurs.

BRIEF SUMMARY OF THE INVENTION

The invention is directed to a method and apparatus for creating an enhanced optical environment for a mounted sensing system used for sensing properties of transparent materials, such as glass such as the thickness of the material and the presence and surface location of any coatings on the material. The invention applies to a vertically-mounted sensing system located beneath a material conveyor system at a defined sensing range from the transparent material under test. The system uses a laser beam (or other directed light source) that travels at an angle up to the surface of the transparent material under test and is reflected back to the sensing system. According to the invention, the sensing system is protected by a thin environmental-protecting layer which transmits the direct and the reflected optical energy without significant distortion. The protective layer may include a hydrophobic coating that does not significantly affect the reflected signal, or the protective material itself may be made of a hydrophobic material. The hydrophobic properties reduce the surface adhesion properties of any contaminants, thus allowing the contaminants to be easily removed by a flow of clean air over the surface. The protective system is further enhanced by an air delivery system which directs a flow of clean air across the signal transmitter and receiver areas and/or the laser reflection receiving area to remove air particulates, liquids and any residue that have landed on the protective layer above the sensor sensor. The clean air flow between the sensor and the material under test also will remove dust and other particulates that otherwise would be in the path of the light beam and its reflection.

The invention may be used in an environment that is wet. The sensor and the protective layer may be splashed or dripped on with water or other liquid cleaning solutions on the surface of the material under test. Because of this, it is necessary to create a water-resistant seal between the protective layer and the sensor enclosure. A water resistant adhesive is used to seal the protective layer to the sensor enclosure, despite any contours or openings in the enclosure itself.

Various objects and advantages of the invention will become apparent from the following detailed description of the invention and the accompanying drawings.

DETAILED DESCRIPTION OF THE INVENTION

Figure 1:
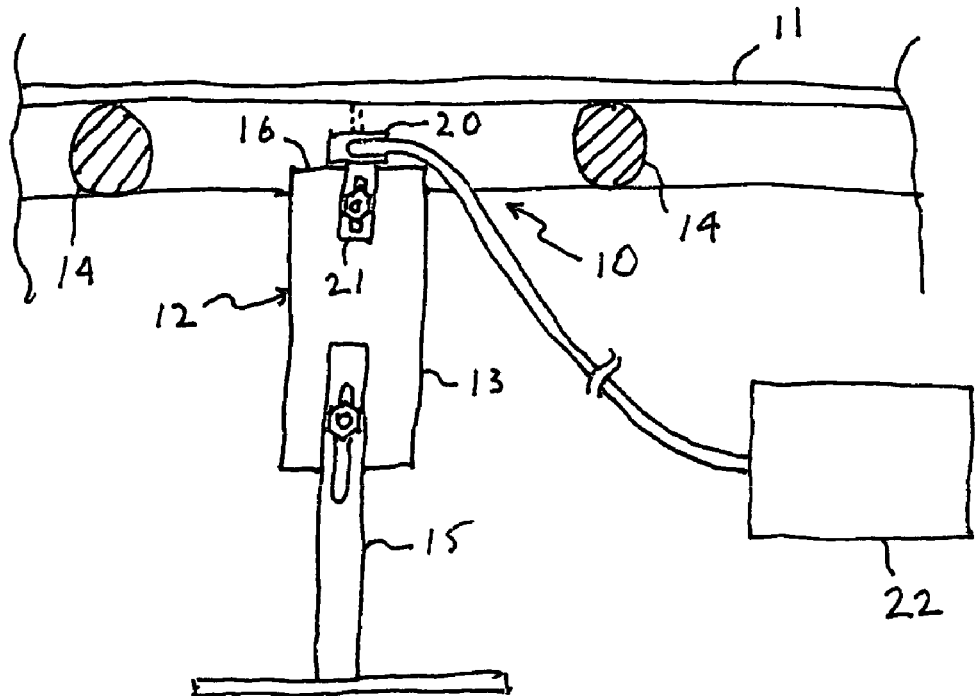
FIG. 1 is a front side elevational view of a system according to the invention in which a glass property sensor which is mounted below a sheet of glass or other transparent material moving on a conveyor is kept clean by a flow of clean air directed over a protective layer mounted on the sensor.
Figure 2:
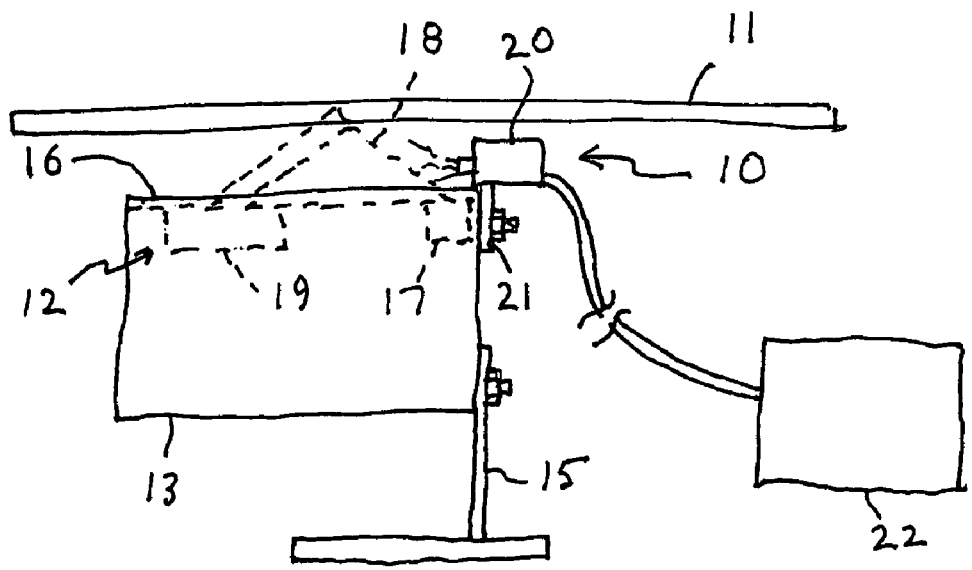
FIG. 2 is a left side elevational view of the system of FIG. 1.

FIGS. 1 and 2 show a signal preservation system for apparatus 10 which measures a property of a sheet of glass 11 or other transparent material, such as the thickness of the glass 11 and/or the presence and surface location of a surface coating. The apparatus includes a conventional sensing apparatus 12 which is mounted in a housing 13. The glass 11 is shown supported on rollers 14 and may be either stationary or moving. The housing 13 is mounted on an adjustable bracket 15 to allow positioning an upper transparent upper housing surface 16 between the rollers 14 at a predetermined distance below the glass 11. The upper housing surface 16 may extend across the entire top of the housing 13, or it may cover an opening in the top of the housing 13 which has an area less that the area of the entire top of the housing 13. As shown in FIG. 2, the sensing apparatus 12 includes a light source 17, which is preferably a laser, and a sensor 19 which is an array of sensors capable of sensing the location and strength of each reflection. The light source 17 directs a beam 18 at the glass 11 at a predetermined angle less than 90° so that glass surface reflections back to the sensor 19 are spaced from the light source 17.

The sensor 19 is located in the housing 13 for detecting the location and intensity of each light beam reflection from the glass 11. It should be appreciated that the spacing of a reflection from an upper surface of the glass 11 will be further from the light source 17 than a reflection from the lower surface of a glass, and that the distance between the two reflections may be used to determine the thickness of the glass. It also should be appreciated that as the angle of the light beam 18 to the surfaces of the glass 11 decreases, the spacing between the light source 17 and the sensor 19 will increase and the spacing between bottom and top glass surface reflections will increase. A surface coating on the glass will affect the strength of the reflection from the surface. For example, a LOW E energy efficient surface coating on the glass 11 will have a greater reflectivity than an uncoated surface, resulting in a stronger signal. Consequently, a comparison of the strengths of reflections from two surfaces will show the presence and location of any surface coatings. Sensing apparatus 12 of the type described is well known in the art and is commercially available. However, the sensing apparatus 12 has not been mounted below the material under test in a housing providing a protective layer 16, and an air flow to clean the protective layer 16.

According to one aspect of the invention, an air nozzle 20 is mounted on an adjustable bracket 21, which preferably is attached to the housing 13. A pressurized and filtered air source 22 supplies a flow of clean air to the air nozzle 20. The air source 22 may be, for example, filtered compressed shop air which is normally available in manufacturing plants, or a separate compressor and filter. The position and orientation of the nozzle 20 is adjusted to direct a stream of clean air to flow over the upper surface 16 and to flow between the upper surface 16 on the housing and the glass 11. The air flow eliminates any dust particles in the transmission path for the light beam 18 and the surface reflections from the glass 11 to provide strong, undistorted reflections at the sensor 19. The air flow also will blow any loose particles from the upper housing surface 16. The air stream pattern should have sufficient velocity to be effective in removing water, Lucor (a separating powder used between layers of glass), and any other liquid and solid contaminents found in a typical production environment. The air nozzle 20 may have an adjustable pattern and may include a flow control valve to adjust the discharge air flow rate from the nozzle 20.

According to a second embodiment of the invention, the transparent upper surface 16 of the sensor housing 13 is either formed from a hydrophobic material or is a sheet of transparent material, such as glass or plastic, coated with a hydrophobic coating such that the exposed surface has hydrophobic properties which repel liquids, dust and other particles. Hydrophobic transparent plastic materials are known in the art and optical grade transparent hydrophobic coatings are used, for example, on eyeglass lenses. These hydrophobic coatings do not significantly change the optical characteristics of the eyeglass lenses. They are effective for combating the buildup of water, grease and dirt on the lenses. The hydrophobic properties of the coating or of the material are effective to cause liquid drops to bead up on the upper surface 16 so that it is more easily removed from the surface 16 by the air flow from the air nozzle 20. Preferably, the hydrophobic properties of the surface 16 are such as to provide a high contact angle for liquid droplets and a low surface energy so that water and other liquid droplets readily bead up and easily roll off of the surface 16 under the influence of the air flow. Materials having these properties are used, for example, to coat some eyeglass lenses, and are sometimes referred to as "easy-clean" coatings.

The housing 13 for the sensing apparatus 12 may be made, for example, from metal or a strong plastic. The upper surface 16 may be of glass or of a transparent plastic which is sealed around its perimeter to the rest of the housing 13 with a suitable water resistant adhesive to prevent entry of liquid, dust and other contaminants into the housing 13. The upper surface 16 should not significantly diminish or affect the quality of the laser beam reflections from the glass 11 and should not allow additional reflections to appear from light bouncing inside the glass 11 that will diminish the measurements.

The material forming the upper housing surface 16 also should be of sufficient strength to physically protect the sensing apparatus 12 from being damaged if any material is dropped onto the surface 16. It is likely that broken glass or tools used by mechanics on a production line could be dropped between the rollers 14. Optical filters used in the sensing apparatus 12 are extremely fragile and can be easily damaged by falling debris. The housing surface 16 should provide sufficient surface strength to withstand the falling debris to protect the optical filters, without breaking itself.

It will be appreciated that various modifications and changes may be made to the above described preferred embodiment of without departing from the scope of the following claims. Although a specific type of optical sensing apparatus 12 has been described, the invention is applicable to other types of optical sensors. In the drawings, the housing 13 is shown on an adjustable support bracket 15 and the air nozzle 20 is shown mounted on the housing with an adjustable mounting bracket 21. These are illustrated as being of the type in which a bolt extends through an elongated slot. After the housing 13 or the air nozzle 20 is positioned, a nut is tightened to secure the position of the housing 13 or of the air nozzle 20. It will be appreciated that other known mounts may be used without departing from the scope of the invention.

The invention claimed is:

1. Apparatus for optically sensing a property of a sheet of transparent material supported on spaced rollers, said apparatus comprising:
    sensor apparatus including a light beam source and a sensor for detecting the location and strength of reflections of the light beam from a sheet of transparent material,
    a housing enclosing said sensor apparatus, said housing having an upper opening through which the light beam and light beam reflections from a sheet of transparent material pass,
    a transparent member covering said upper opening, and
    an air nozzle mounted to direct a flow of air over an upper surface of said transparent member to remove particles and liquid from said upper surface.

2. Apparatus for sensing a property of a sheet of transparent material, as set forth in claim 1, and wherein said transparent member is formed from a hydrophobic material.

3. Apparatus for sensing a property of a sheet of transparent material, as set forth in claim 2, and wherein said transparent member is sealed to said housing with a water resistant adhesive.

4. Apparatus for sensing a property of a sheet of transparent material, as set forth in claim 1, and wherein said upper surface of said transparent member is coated with a hydrophobic material.

5. Apparatus for sensing a property of a sheet of transparent material, as set forth in claim 4, and wherein said transparent member is sealed to said housing with a water resistant adhesive.

6. Apparatus for sensing a property of a sheet of transparent material, as set forth in claim 1, and wherein said air nozzle is adjustably mounted on said housing.

* * * * *